United States Patent
Mangum et al.

(10) Patent No.: US 7,972,515 B1
(45) Date of Patent: Jul. 5, 2011

(54) IN SITU MEMBRANE INTEGRITY TEST

(75) Inventors: Scott R. Mangum, Bethesda, MD (US); John J. Lawson, Severn, MD (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 315 days.

(21) Appl. No.: 12/287,727

(22) Filed: Oct. 10, 2008

(51) Int. Cl.
- *C02F 1/44* (2006.01)
- *G01N 15/08* (2006.01)
- *G01M 3/04* (2006.01)

(52) U.S. Cl. .............. 210/650; 210/321.65; 210/321.69; 73/38; 73/40

(58) Field of Classification Search .......... 210/321.65, 210/321.69, 696, 745, 94, 96.2, 143, 198.1, 210/321.6, 636, 639, 650–653; 436/169, 436/172, 55, 56, 164, 162; 422/14, 62, 92.05, 422/82.08, 82.09; 73/37–38, 40
See application file for complete search history.

(56) References Cited

U.S. PATENT DOCUMENTS

| | | | |
|---|---|---|---|
| 3,392,573 A * | 7/1968 | Benson et al. | 73/38 |
| 4,324,568 A * | 4/1982 | Wilcox et al. | 95/286 |
| 4,515,007 A * | 5/1985 | Herman | 73/38 |
| 4,872,974 A | 10/1989 | Hirayama et al. | |
| 5,282,380 A * | 2/1994 | DiLeo et al. | 73/38 |
| 5,507,959 A * | 4/1996 | Glick | 210/797 |
| 5,844,406 A | 12/1998 | Gormley et al. | |
| 6,254,787 B1 * | 7/2001 | Kimura et al. | 73/1.02 |
| 6,361,695 B1 | 3/2002 | Husain et al. | |
| 6,838,002 B2 * | 1/2005 | Zeiher et al. | 210/650 |
| 6,983,504 B2 * | 1/2006 | Grummert et al. | 73/38 |
| 7,040,512 B2 | 5/2006 | Tanny et al. | |
| 7,698,928 B2 * | 4/2010 | Jons et al. | 73/38 |
| 2004/0226898 A1 * | 11/2004 | Halstead et al. | 210/798 |
| 2006/0188994 A1 * | 8/2006 | Ding et al. | 436/3 |
| 2007/0079649 A1 * | 4/2007 | Nauseda et al. | 73/40 |
| 2008/0110243 A1 * | 5/2008 | Burke et al. | 73/38 |

* cited by examiner

*Primary Examiner* — Tony G Soohoo
*Assistant Examiner* — David C Mellon
(74) *Attorney, Agent, or Firm* — Dave A. Ghatt

(57) ABSTRACT

An in situ reverse flow shipboard membrane integrity test apparatus and method, for determining if a membrane arrangement is defective. A membrane arrangement within a separation unit is tested when the membrane arrangement is arranged to perform wastewater separating functions. The separation unit includes a first inlet conduit, a first outlet conduit, and a second outlet conduit. An end cap is attached to the second outlet conduit to seal the second outlet conduit. A test air supply connected to the first outlet conduit for supplying an airflow to the membrane and a microparticle source containing microparticles for injecting microparticles into the airflow forming a test airflow. The test airflow is directed towards the membrane, and a filter is positioned over the first inlet conduit. The presence or absence of microparticles on the filter indicates whether or not the membrane arrangement is defective.

17 Claims, 2 Drawing Sheets

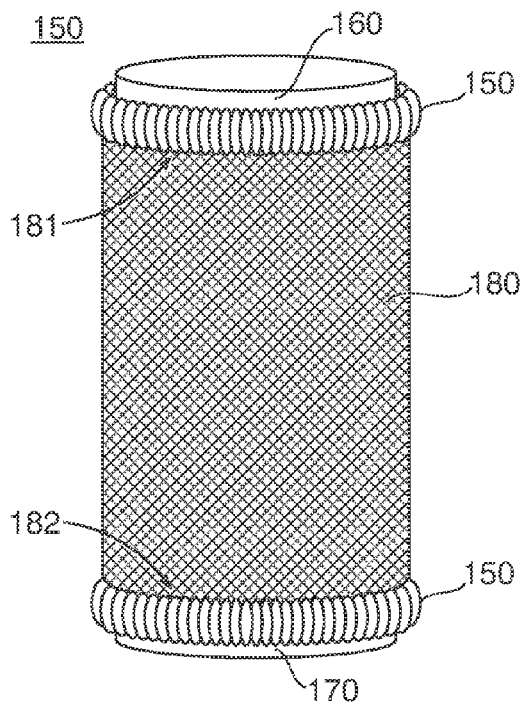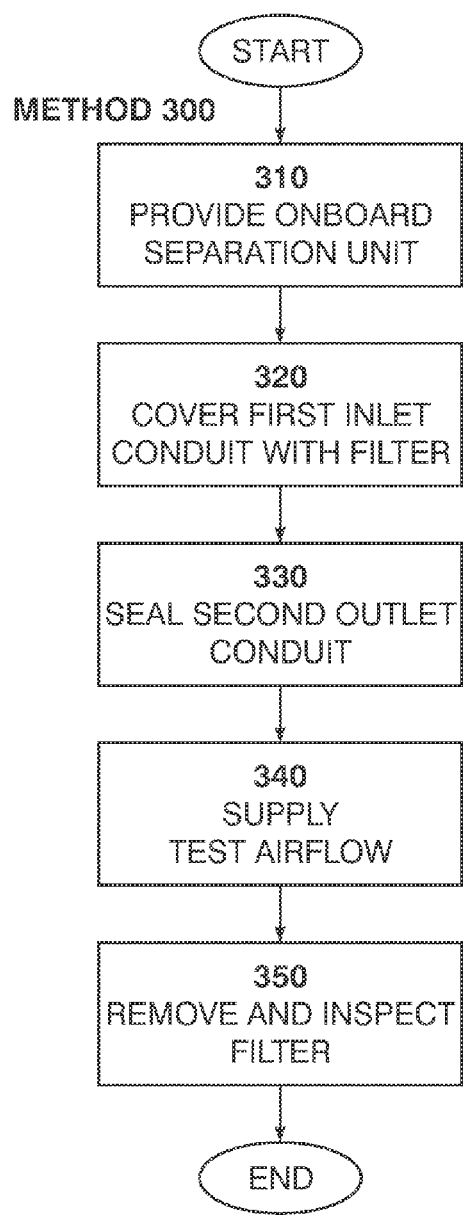

IN SITU MEMBRANE INTEGRITY TEST

STATEMENT OF GOVERNMENT INTEREST

The following description was made in the performance of official duties by employees of the Department of the Navy, and, thus the claimed invention may be manufactured, used, licensed by or for the United States Government for governmental purposes without the payment of any royalties thereon.

TECHNICAL FIELD

The following description relates generally to an apparatus and method for testing the integrity of a membrane, and in particular, an in situ arrangement and method to quickly test the integrity of a membrane of a separation unit.

BACKGROUND

The Navy has developed onboard water treatment systems that can be implemented in military and non-military applications. One such treatment system is the ceramic membrane ultrafiltration oily waste membrane system. These systems are very effective and have been shown to produce an effluent that has an oil concentration consistently below 15 ppm.

The filtering member/membrane requires frequent replacement as routine maintenance. Replacement membranes are typically packaged and shipped to the fleets for installation. The packaging, shipping, and installation of typically large, expensive, heavy, and brittle ceramic filtration membranes can cause cracking in the membrane. When installed, the membrane is a vital part of the functioning waste water treatment system. If a membrane is cracked or a seal is compromised the entire system fails. Untreated water may pass through a crack in the membrane or via a defective membrane seal, allowing waste laden water to be released to the clean water side of the system. A method and arrangement for determining the membrane integrity before commissioning the membrane with waste water is desired. Additionally, an in situ arrangement for determining the integrity is desired.

SUMMARY

In one aspect, the invention is a reverse flow shipboard membrane integrity test system. The test system includes a separation unit having a one or more outer walls, and a first inlet conduit for feeding wastewater into the separation unit for treatment thereat. The separation unit of the system further includes a first outlet conduit for discharging filtered water separated from the wastewater, and a second outlet conduit for discharging concentrated liquid waste separated from the wastewater. The separation unit further includes a membrane arrangement positioned within the one or more outer walls, positioned for separating the wastewater into the filtered water and the concentrated liquid waste. In this aspect, the reverse flow shipboard membrane integrity test system also includes an end cap attached to the second outlet conduit sealing the second outlet conduit. An air supply is connected to the first outlet conduit for supplying an airflow to the membrane, and a microparticle source containing microparticles is connected to the first outlet conduit for injecting microparticles into the airflow forming a test airflow. In this aspect the test airflow is directed towards the membrane and a filter positioned over the first inlet conduit for collecting microparticles thereon.

In another aspect, the invention is a reverse flow shipboard membrane integrity test method. The method includes the providing of an onboard separation unit having one or more outer walls, and a first inlet conduit for feeding wastewater into the separation unit for treatment thereat. The separation unit is also provided with a first outlet conduit for discharging filtered water separated from the wastewater, and a second outlet conduit for discharging concentrated liquid waste separated from the wastewater. The separation unit is further provided with a membrane arrangement positioned within the one or more outer walls for separating the wastewater into the filtered water and the concentrated liquid waste. In this aspect the method further includes covering the first inlet conduit with a filter, and sealing the second outlet conduit. The method further includes supplying a test airflow having microparticles therein to the membrane arrangement, via the first outlet conduit. In this aspect the reverse flow shipboard membrane integrity test method includes the removing and inspecting of the filter after supplying the test airflow to determine if the membrane arrangement is defective or intact. The membrane arrangement is defective if microparticles are visibly discernable on the filter and intact if microparticles are not visibly discernable on the filter.

BRIEF DESCRIPTION OF THE DRAWINGS

Other features will be apparent from the description, the drawings, and the claims.

FIG. 2 is a perspective illustration of a membrane arrangement, according to an embodiment of the invention.

FIG. 3 is a flowchart illustrating a reverse flow shipboard membrane integrity test method, according to an embodiment of the invention.

DETAILED DESCRIPTION

Figure 1A:
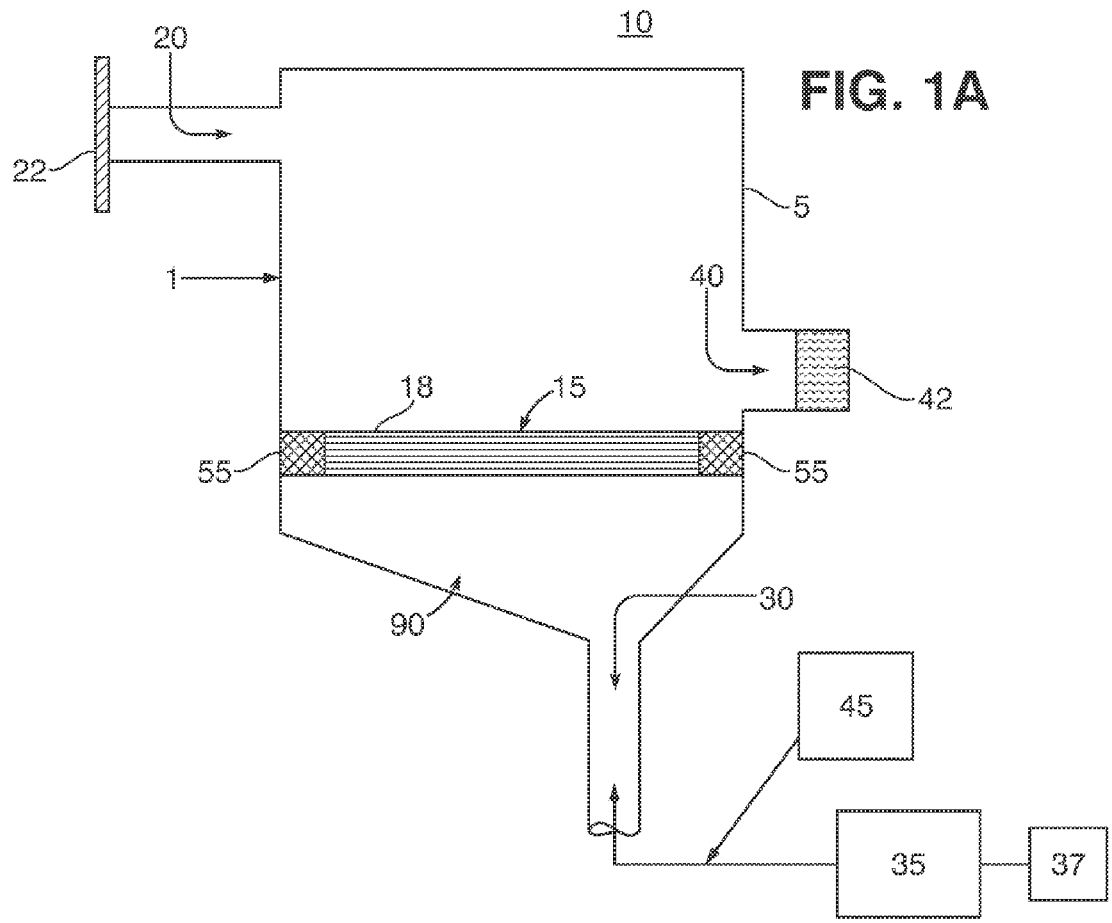
FIG. 1A is a schematic illustration of an in situ membrane integrity test system, according to an embodiment of the invention

FIG. 1A is a sectional schematic illustration of an in situ membrane integrity test system 10, according to an embodiment of the invention. As will be outlined below, the system 10 is used to in situ test a membrane arrangement of a wastewater treatment system. The wastewater treatment system may be for example, a shipboard system or a land-based system, and may treat black water, gray water, bilge water, or the like.

As shown in FIG. 1A, the in situ membrane integrity test system 10 includes a separation unit 1 having one or more outer walls 5, and a filtration membrane arrangement 15. The membrane arrangement 15 includes a membrane 18 and one or more sealing members 55, which are positioned between the membrane 18 and the one or more outer walls to provide an airtight seal between the members. As shown, the membrane 18 is planar. The membrane 18 may be a ceramic material, may be multilayered, and may vary in surface area, thickness, size of lumen holes, length, and pressure resistance. The shape of the membrane arrangement 15 is complementary with the shape of the one or more outer walls 5. Thus, both the one or more outer walls 5, and the membrane arrangement 15 may be any desired shape, such as rectangular, cylindrical, or irregular. The one or more sealing members 55 of the membrane arrangement 15 may circumscribe the membrane 18 along an outer edge of the membrane, and may comprise an elastomeric material.

The separation unit 1 includes an inlet conduit 20 for introducing wastewater into the unit for treatment thereof. The unit also includes a first outlet conduit 30 for discharging liquids filtered by the membrane 18. A second outlet conduit 40 is provided for discharging concentrated liquid waste separated by the membrane 18.

The system 10 is provided to test the integrity of the membrane arrangement 15, when the membrane arrangement 15 is in an operating position within the separation unit 1. As shown in FIG. 1A, the system 10 includes an air supply 35 attached to the first outlet conduit 30. The air supply 35 provides air directly to the membrane arrangement 15 via the first outlet conduit 30. FIG. 1A also illustrates a microparticle source 45 for injecting microparticles into air provided by the air supply 35. The microparticles from the source 45 are entrained in the air forming a test airflow which bombards the membrane arrangement 15. The pressure at which the test airflow is directed through the first outlet conduit 30 is controlled a pressure regulator 37 connected to the air supply 35.

The system 10 also includes an end cap 42 for sealing shut the second outlet conduit. The system 10 further includes a filter 22 which is positioned over the inlet conduit 20. In operation, the microparticles of the test airflow strike the membrane arrangement 15. If the membrane arrangement 15 is defective, i.e., if the membrane 18 or one or more sealing members 55 include gaps or breaks, microparticles penetrate the gaps or breaks, and are collected on the filter 22. If the membrane arrangement 15 is intact, the microparticles rebound off the filter 22 and settle in the inlet region 90. After testing, the filter 22 may be removed by an observer for inspection. The presence of microparticles on the filter 22 indicates that the membrane 15 is defective. A clean filter 22 indicates that the membrane 15 is intact.

Figure 1B:
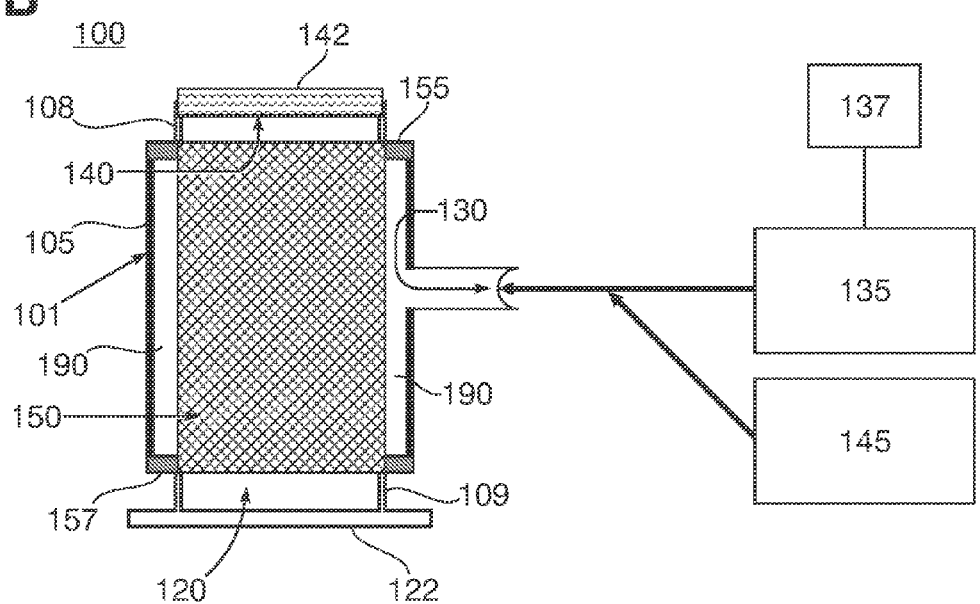
FIG. 1B is a schematic illustration of an in situ membrane integrity test system, according to an embodiment of the invention.

FIG. 1B is a schematic illustration of an in situ membrane integrity test system 100, according to another embodiment of the invention. Similar to the system 10 above, the in system 100 is used to in situ test a membrane arrangement of a wastewater treatment system. As stated above, the wastewater treatment system may be for example, a shipboard system or a land-based system, and may treat black water, gray water, bilge water, or the like. The in situ membrane integrity test system 100 includes a separation unit 101.

The separation unit 101 may have a substantially cylindrical outer wall 105, and a substantially hollow cylindrical membrane arrangement 150 within the outer wall 105. FIG. 2 is a perspective illustration of a membrane arrangement 150, according to an embodiment of the invention. The cylindrical membrane includes an upper ring-shaped support member 160 and a lower ring-shaped support member 170. A membrane 180 having an upper end 181 supported on the upper ring-shaped support member 160, and a lower end 182 supported on the lower ring-shaped support member 170. As shown, the membrane arrangement 150 takes the form of a hollow open-ended cylinder.

The membrane 180 may be ceramic and may be formed from materials such as silica, alumina, zirconia, silicon carbide, silicon nitride, titania, titanium nitride, silicon glass, combinations thereof, and the like. Pores in the membrane generally have pore sizes ranging from 0.01 to 50 microns, although other values outside this range may be employed. Each pore in the membrane may have a size that is substantially equal to the size of every other pore in the membrane. The composition and structure, including the porosity, of the membrane is selected according to the application. As the case with the membrane 18, the membrane 180 may be multilayered, may vary in surface area, thickness, size of lumen holes, length, and pressure resistance. FIG. 2 shows the membrane arrangement 150 having sealing members 155 and 157, which may be O-rings. The sealing members 155 and 157 are located over the upper and lower support members 160 and 170 respectively, and are used to provide an airtight seal with the substantially cylindrical outer wall 105 of the separation unit 101. FIG. 1B shows the airtight sealing arrangement. The membrane arrangement 150 may be held in position within the outer wall 105 by the snug elastic fit provided by the sealing members 155 and 157. Pressure distribution within the separation unit 101 may also contribute to the strength of the airtight seal. Additionally, either or both of the upper and lower ring-shaped members 160 and 170 may be provided with threaded areas to mate with corresponding threaded areas on the wall of the separation unit 101. FIG. 1B shows possible threaded regions 108 and 109 where threads on the separation unit and threads on upper and lower support members 160 and 170 have a mating relation.

As shown in FIG. 1B, the separation unit 101 also includes an inlet conduit 120 at a lower end of the separation unit 101. The separation unit 101 also includes a first outlet conduit 130 extending through the substantially cylindrical outer wall 105, and a second outlet conduit 140 at an upper end of the separation unit 101. The in situ membrane integrity test system 100 also includes an air supply 135 attached to the first outlet conduit 130. The air supply 135 provides air to the separation unit via the first outlet conduit 130. The air supply 135 is attached to a pressure regulator 137 for regulating the pressure at which the air is fed. FIG. 1B also shows a microparticle source 145, which injects microparticles into the air stream created by the air supply 135 and pressure regulator 137. Thus, the microparticles are entrained forming a test airflow, which as outlined below, is used to test the integrity of the membrane arrangement 150. The microparticles may be any desired shape and size. For example, the microparticles may be glass bead microspheres of the order of about 500 microns, or garnet powder microspheres of the order of about 15 microns, or other particles having sizes between about 500 microns and about 10 microns. It should be noted that each microparticle in the microparticle source 145 may have a size that is substantially equal to the size of every other microparticle in the source 145.

The system 100 also includes an end cap 142, which as outlined below, seals the second outlet, preventing the leakage of air during the membrane integrity testing. The system 100 further includes a filter 122 positioned over the inlet 120 for collecting microparticles. The filter may be made from cloth material such as linen, cotton, polyester, and combinations thereof selected to aid in detection of the inert beads. The filter may be held over the inlet 120 by means of a clamping device, adhesives, or combinations thereof.

The system 100 as outlined above has the capability of testing the membrane arrangement 150 when the membrane arrangement is set up to perform wastewater treatment functions. During wastewater treatment functions, when the membrane integrity system 100 is not being employed, system elements such as the filter 122, the end cap 142, the air supply 135, the pressure regulator 137, and the microparticle source 145 are not provided in the arrangement. Instead, the first inlet conduit 120 is attached to a wastewater source, supplying wastewater to be processed by the membrane arrangement 150. The wastewater is processed and separated into an environmentally friendly water product, and a liquid concentrate waste product. The environmentally friendly water product is filtered from wastewater inside the hollow of the membrane arrangement 150, and under pressure, seeps through the membrane 180 to the outside of the membrane arrangement 150. The filtered water product then exits the separation unit via the first outlet conduit 130 which is attached to an evacuation source to evacuate the filtered water. The liquid concentrate waste product exits via the second outlet conduit 140, which is also attached to an evacuation source. The in situ membrane integrity test system 100, may be set up to test for breaks and in the membrane arrangement, which includes breaks in the seal, before or between wastewater treatment runs.

As outlined above, the system 100 includes an air supply 135 and a microparticle source 145 attached to the first outlet conduit 130. The system also includes an end cap 142 sealing the second outlet conduit 140, and a filter 122 positioned over the inlet 120. In operation, the in situ membrane integrity test system 100 operates as follows. A test airflow, created when microparticles from source 145 is injected into an air stream from source 135, is directed into the first outlet conduit 130 towards the membrane arrangement 150. The pressure regulator controls the pressure at which the test airflow is applied, maximizing results without damaging the membrane 180. The test airflow may be applied at pressures between about 10 psi and about 100 psi, depending on the strength of the membrane layer. In one particular embodiment, the test airflow is imparted at about 30 psi.

The test airflow which includes microparticles impinges on the membrane arrangement 150. If the membrane 180 of the arrangement 150 is cracked or broken, microparticles in the test airflow pass though the broken or cracked regions, and eventually come to rest on the filter 122 at the inlet 120. The membrane arrangement 150 may also be breached via improper seals 155 and 157, if the seals are not properly arranged in the separation unit 101. Microparticles that breach the membrane arrangement via the seals 150, are also captured on the filter 122. If the integrity of the membrane arrangement 150 is intact, then the microparticles bounce off the arrangement and settle in an outflow region 190. The outflow region 190 is generally the sealed region between the membrane arrangement 150 and the substantially cylindrical outer wall 105.

The filter can be withdrawn and inspected for microparticles to determine if the membrane arrangement 150 is defective or intact. The presence of any microparticles on the filter 122 indicates that the membrane arrangement 150 is defective. If it is determined that the membrane arrangement 150 is defective, the defective membrane arrangement 150 may be replaced with a new arrangement 150, which may be tested for its integrity. If it is determined by the absence of microparticles that the membrane arrangement 150 is intact, then the air supply 135 and microparticle source 145 may be disconnected from the first outlet conduit 130, and replaced with an evacuation device. Similarly, the end cap 142 may be removed from the second outlet conduit 140, and replace with another evacuation device. A wastewater supply may be attached to the inlet conduit 120, after which, wastewater processing may commence. During the wastewater treatment, the environmentally friendly microparticles are flushed out of the system along with filtered water.

As outlined above, the microparticles may be glass bead microspheres of the order of about 500 microns, or garnet powder microspheres of the order of about 15 microns, or other inert particles having sizes between about 500 microns and about 10 microns. The size of the microparticles is selected based on the size of membrane pores and visibility. As stated above, the membrane 180 may have a pore size that may be less than 1 micron, and generally in the range of about 0.01 micron to about 50 microns, although other values outside this range may be employed. Thus for example, larger microspheres of the order of about 500 microns may be employed when testing a membrane of the order of about 50 microns. Additionally, the microparticles may be dyed to have bright colors that are easily discernable on the filter. Microparticles may be dyed to be florescent or may be coated with luminous chemicals to enhance visibility. Additionally, the filter may also be colored to provide a greater contrast between the microparticles and the filter.

It should be noted that system 100 is similar to system 10, and corresponding elements may have similar physical characteristics, including similar dimensions and materials. For example, the microparticles of system 10 may be glass bead microspheres of the order of about 500 microns, or garnet powder microspheres of the order of about 15 microns, or other inert particles having sizes between about 500 microns and about 10 microns. Also, the membrane 15 of system 10 may have a pore size that may be less than 1 micron, and generally in the range of about 0.01 micron to about 50 microns. Additionally, testing conditions may also be similar. Thus the pressure regulator 37 may introduce the test airflow at pressures of about 10 psi to about 100 psi.

FIG. 3 is a flowchart illustrating a reverse flow shipboard membrane integrity test method 300, according to an embodiment of the invention. The steps involved in the method 300 of testing the integrity of a membrane arrangement have been outlined above in reference to FIGS. 1A, 1B, and 2. FIG. 3 merely provides a broad overview of the method 300. For example, according to the method, step 310 is the providing an onboard separation unit (1, 101). As shown in FIGS. 1A and 1B the separation unit (1, 101) includes a first inlet conduit (20, 120) for feeding wastewater into the separation unit for treatment thereat, a first outlet conduit (30, 130) for discharging water separated from the wastewater, and a second outlet conduit (40,140) for discharging concentrated liquid waste separated from the liquids. The separation unit (1, 101) is also provided with a membrane arrangement (15, 150) for separating the wastewater into the filtered water and the concentrated liquid waste.

Step 320 is the covering the of first inlet conduit (20, 120) with a filter (22, 122). As outlined above the filter may be held over the inlet by means of a clamping device, adhesives such as hook and loop arrangements, or combinations thereof. Step 330 is the sealing the of second outlet conduit (40, 140). The second outlet conduit (40, 140) may be sealed with an end cap (42,142), which prevents the escape of gases during the membrane integrity testing process. Step 340 is the supplying of a test airflow having microparticles therein to the membrane arrangement (15, 150). The test airflow is supplied via the first outlet conduit (30, 130).

Step 350 is the removing and inspecting of the filter (22, 122) after supplying the test airflow, to determine if the membrane arrangement (15, 150) is defective or intact. As outlined above, if the membrane (18, 180) of the arrangement (15, 150) is cracked or broken, microparticles in the test airflow pass though these openings, and eventually come to rest on the filter (22, 122). Microparticles may also breach the membrane arrangement (15, 150) via gaps in the sealing arrangement. By inspecting the filter (22, 122), an observer can determine if the membrane arrangement 150 is defective or intact. The membrane arrangement (15, 150) is defective if microparticles are visibly discernable on the filter (22, 122), and intact if microparticles are not visibly discernable on the filter.

It should be noted that according to the method 300, if it is determined that the membrane arrangement (15, 150) is defective, the membrane arrangement may be replaced with another membrane arrangement (15, 150), which may then be tested. Also, if the tested membrane arrangement (15, 150) is determined to be intact, wastewater treatment may commence. Thus, the filter (22, 122), the end cap (42, 142), and the air supply (35, 135) and microparticle sources (45, 145) are removed, and a supply of wastewater is connected to the first inlet conduit (20, 120), and evacuation sources connected to the first and second outlet conduits (30, 130) and (40, 140), respectively.

What has been described and illustrated herein are preferred embodiments of the invention along with some variations. The terms, descriptions and figures used herein are set forth by way of illustration only and are not meant as limitations. For example, the membrane may be multilayered, may vary in surface area, thickness, size of lumen holes, length, pressure resistance, and shape. Thus, although the membrane is illustrated as being planar in one instance, and cylindrical in another, the membrane may be any desired shape, such as cubic, or irregular for example. Additionally, method steps may take place in various orders. Those skilled in the art will recognize that many variations are possible within the spirit and scope of the invention, which is intended to be defined by the following claims and their equivalents, in which all terms are meant in their broadest reasonable sense unless otherwise indicated.

What is claimed is:

1. A reverse flow shipboard membrane integrity test system comprising:
    a separation unit comprising:
    one or more outer walls;
    a first inlet conduit for feeding wastewater into the separation unit for treatment thereat;
    a first outlet conduit for discharging filtered water separated from the wastewater;
    a second outlet conduit for discharging concentrated liquid waste separated from the wastewater;
    a membrane arrangement positioned within the one or more outer walls positioned for separating the wastewater into the filtered water and the concentrated liquid waste;
    an end cap attached to the second outlet conduit, sealing the second outlet conduit;
    an air supply connected to the first outlet conduit for supplying an airflow to the membrane;
    a microparticle source containing microparticles connected to the first outlet conduit and the air supply, for injecting microparticles into the airflow forming a test airflow, wherein the test airflow is directed towards the membrane; and
    a filter positioned over the first inlet conduit for collecting microparticles thereon.

2. The system of claim 1, wherein the air supply includes a pressure regulator for regulating the test airflow into the separation unit at pressures of about 10 psi to about 100 psi.

3. The system of claim 2, wherein the one or more outer walls of the separation unit comprises a substantially cylindrical outer wall; and
    wherein the membrane arrangement comprises:
        an upper ring-shaped support;
        a lower ring-shaped support; and
        a cylindrical membrane having an upper end and a lower end, the upper end of the cylindrical membrane supported on the upper ring-shaped support, and the lower end of the cylindrical membrane supported on the lower ring-shaped support, forming a hollow cylindrical arrangement.

4. The system of claim 3, wherein the membrane arrangement further comprises:
    an upper O-ring positioned around the upper ring-shaped housing support; and
    a lower O-ring positioned around the lower ring-shaped housing support, wherein each of the upper and the lower O-rings press against the substantially cylindrical outer wall to form an airtight relationship between the membrane arrangement and the substantially cylindrical outer wall.

5. The system of claim 4, wherein in the separation unit, the first inlet is located at a lower end of the separation unit, the first outlet is located in the substantially cylindrical outer wall, and the second outlet is located at an upper end of the separation unit.

6. The system of claim 5, wherein in the microparticle source, each microparticle has a substantially similar size to every other microparticle, in the order of about 10 microns to about 500 microns.

7. The system of claim 2, wherein the membrane arrangement comprises:
    a substantially flat membrane; and
    one or more sealing members circumscribing an outer edge of the substantially flat membrane, the one or more sealing members for providing an airtight seal between the membrane and the one or more outer walls.

8. A reverse flow shipboard membrane integrity test method comprising:
    providing an onboard separation unit comprising:
        one or more outer walls;
        a first inlet conduit for feeding wastewater into the separation unit for treatment thereat;
        a first outlet conduit for discharging filtered water separated from the wastewater;
        a second outlet conduit for discharging concentrated liquid waste separated from the wastewater;
        a membrane arrangement positioned within the one or more outer walls for separating the wastewater into the filtered water and the concentrated liquid waste;
    the method further comprising:
        covering the first inlet conduit with a filter;
        sealing the second outlet conduit;
        supplying a test airflow having microparticles therein to the membrane arrangement, via the first outlet conduit;
        removing and inspecting the filter after supplying the test airflow to determine if the membrane arrangement is defective or intact, wherein the membrane arrangement is defective if microparticles are visibly discernable on the filter and wherein the membrane arrangement is intact if microparticles are not visibly discernable on the filter.

9. The method of claim 8, wherein the supplying of the test airflow having microparticles comprises:
    connecting an air supply to the first outlet conduit to produce an airflow;
    connecting a microparticle source to the test air supply; and
    injecting microparticles from the microparticle source into the airflow.

10. The method of claim 9, wherein the test airflow is supplied at about 10 psi to about 100 psi.

11. The method of claim 10, wherein the microparticles in the test airflow each have a substantially equal size in the order of about 10 microns to about 500 microns, wherein said microparticle size is selected based on the permeability of the membrane.

12. The method of claim 11, wherein the microparticles are brightly colored in a color that contrasts with the color of the filter, so that microspheres on the filter are easily discernable to an observer.

13. The method of claim 12, wherein the membrane arrangement comprises:
- a substantially flat membrane; and
- one or more sealing members circumscribing an outer edge of the substantially flat membrane, the one or more sealing members for providing an airtight seal between the membrane and the one or more outer walls.

14. The method of claim 12, wherein the one or more outer walls comprise a substantially cylindrical outer wall; and wherein the membrane arrangement comprises:
- an upper ring-shaped housing support;
- a lower ring-shaped housing support;
- a cylindrical membrane having an upper end and a lower end, the upper end of the cylindrical membrane supported on the upper ring-shaped housing support, and the lower end of the cylindrical membrane supported on the lower ring-shaped housing support, forming a hollow cylindrical arrangement;
- an upper O-ring positioned around the upper ring-shaped housing support; and
- a lower O-ring positioned around the lower ring-shaped housing support, wherein each of the upper and the lower O-rings press the substantially cylindrical outer wall, wherein when the membrane arrangement is defective, the microparticles from the test airflow penetrate the membrane arrangement and are caught in the filter at the first inlet conduit.

15. The method of claim 14, wherein when the membrane arrangement is intact, the microparticles from the airflow repel off the membrane arrangement and accumulate in the sealed outflow region between the membrane arrangement and the substantially cylindrical outer wall, the method further comprising:
- disconnecting the test airflow supply;
- disconnecting the microparticle supply;
- removing the end cap from the second outlet conduit;
- attaching a shipboard wastewater source to the first inlet conduit feed wastewater into the separation unit for treatment therein;
- attaching a first evacuation source to evacuate from the separation unit water separated from the wastewater and microparticles accumulated in the outflow region; and
- attaching a second evacuation source to evacuate from the separation unit concentrated liquid waste separated from the wastewater.

16. The method of claim 14, wherein when inspection of the filter indicates that the membrane is defective, the method further comprises:
- removing the defective membrane arrangement;
- providing a replacement membrane arrangement;
- providing a clean filter at the first inlet conduit;

supplying a test airflow having microparticles therein to the membrane arrangement, via the first outlet conduit;
- removing and inspecting the filter after supplying the test airflow to determine if the membrane arrangement is defective or intact, wherein the membrane arrangement is defective if microparticles are visibly discernable on the filter and wherein the membrane arrangement is intact if microparticles are not visibly discernable on the filter.

17. The method of claim 10, wherein the test airflow is supplied at about 30 psi.

* * * * *